United States Patent [19]

Sunderland

[11] Patent Number: 5,168,892
[45] Date of Patent: Dec. 8, 1992

[54] ADJUSTABLE CARRYING CASE FOR A FLUID DELIVERY SYSTEM

[75] Inventor: Richard A. Sunderland, St. Charles, Mo.

[73] Assignee: Sherwood Medical Company, St. Louis, Mo.

[21] Appl. No.: 818,194

[22] Filed: Jan. 8, 1992

Related U.S. Application Data

[63] Continuation-in-part of Ser. No. 679,886, Apr. 3, 1991.

[51] Int. Cl.[5] ............................................... F16L 3/00
[52] U.S. Cl. ..................................... 137/343; 417/360; 604/153
[58] Field of Search ................ 417/360, 474; 137/565, 137/343; 128/DIG. 12; 604/153

[56] References Cited

U.S. PATENT DOCUMENTS

| | | | |
|---|---|---|---|
| 3,880,188 | 4/1975 | Oakley, Jr. et al. | 137/577 |
| 4,207,889 | 6/1980 | Oloff et al. | 128/213 R |
| 4,397,639 | 8/1983 | Eschweiler et al. | 604/153 |
| 4,416,595 | 11/1983 | Cromie | 417/476 |
| 4,479,761 | 10/1984 | Bilstad et al. | 417/395 |
| 4,545,783 | 10/1985 | Vaughan | 604/259 |
| 4,688,595 | 8/1987 | Srebnik et al. | 137/343 |
| 4,722,734 | 2/1988 | Kolln | 604/151 |
| 5,011,378 | 4/1991 | Brown et al. | 417/360 |
| 5,057,081 | 10/1991 | Sunderland | 604/153 |

OTHER PUBLICATIONS

Fresenius AG, Frenta-System for Continuous Tube Feeding, Instruction For Use, Date Unknown, 13 pages.
Ross Laboratories, Introducing Flexiflo Companian Enteral Nutrition Pump, Feb. 1988, 2 pages.
Ross Laboratories, Flexiflo Companion Enteral Nutrition Pump Operating Manual, Aug. 1987, pp. 1–16.

*Primary Examiner*—A. Michael Chambers
*Attorney, Agent, or Firm*—Andrew J. Beck; Montgomery W. Smith; Gene B. Kartchner

[57] ABSTRACT

The present invention relates to a support device and carrying case for use with a fluid delivery system which includes a fluid delivery set and an infusion pump. The support device allows simple attachment of various types of fluid delivery sets and infusion pumps thereto and is adapted for use with bed ridden patients in a traditional manner, or for ambulatory patient use. The support device includes a compartment for securely holding an infusion pump and a separate compartment for securely holding a fluid container of the fluid delivery set. The device further includes an elongate channel into which the tubing of the fluid delivery set can be inserted and subsequently protected from kinking or inadvertent occlusion. The support device is adapted for use with rigid bottle, flexible bag, burette, spike sets, or other standard types of fluid delivery sets, and is designed to be adjustable to receive various conformations of the support device depending on the particular type of fluid delivery set container being used.

24 Claims, 9 Drawing Sheets

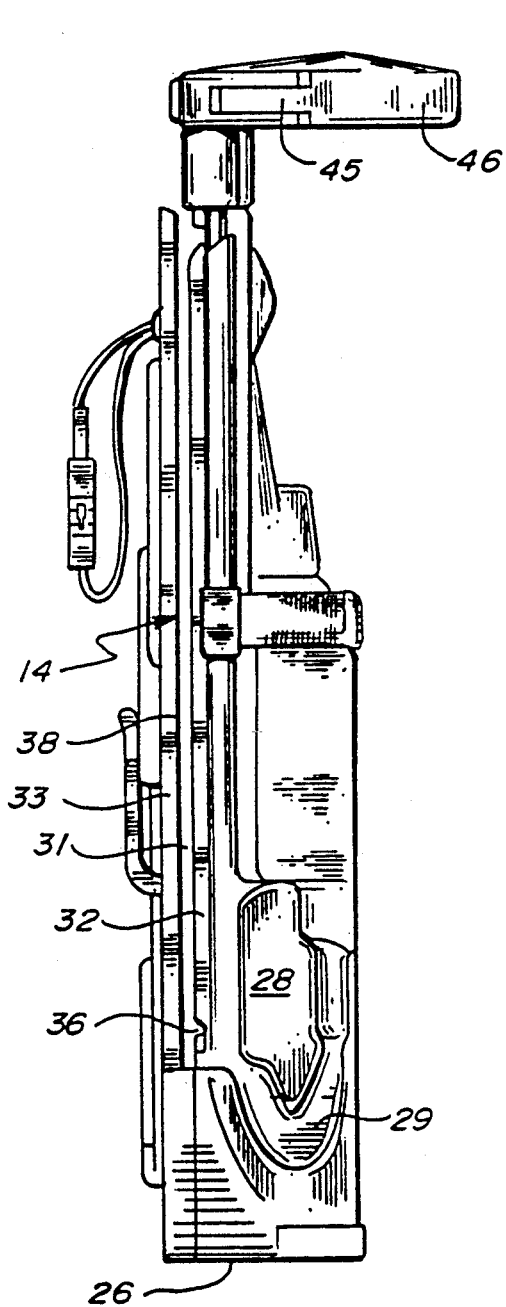
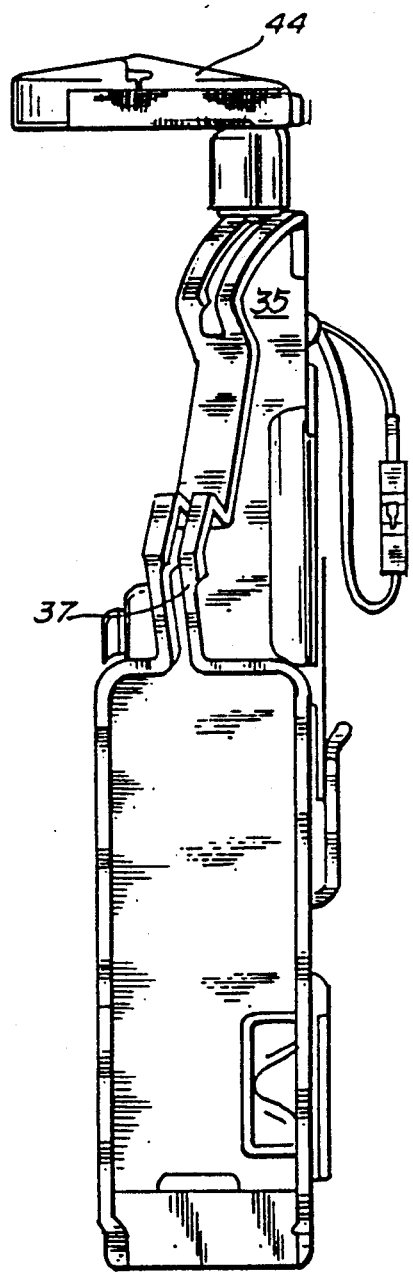
Fig. 1b.
Fig. 1c.

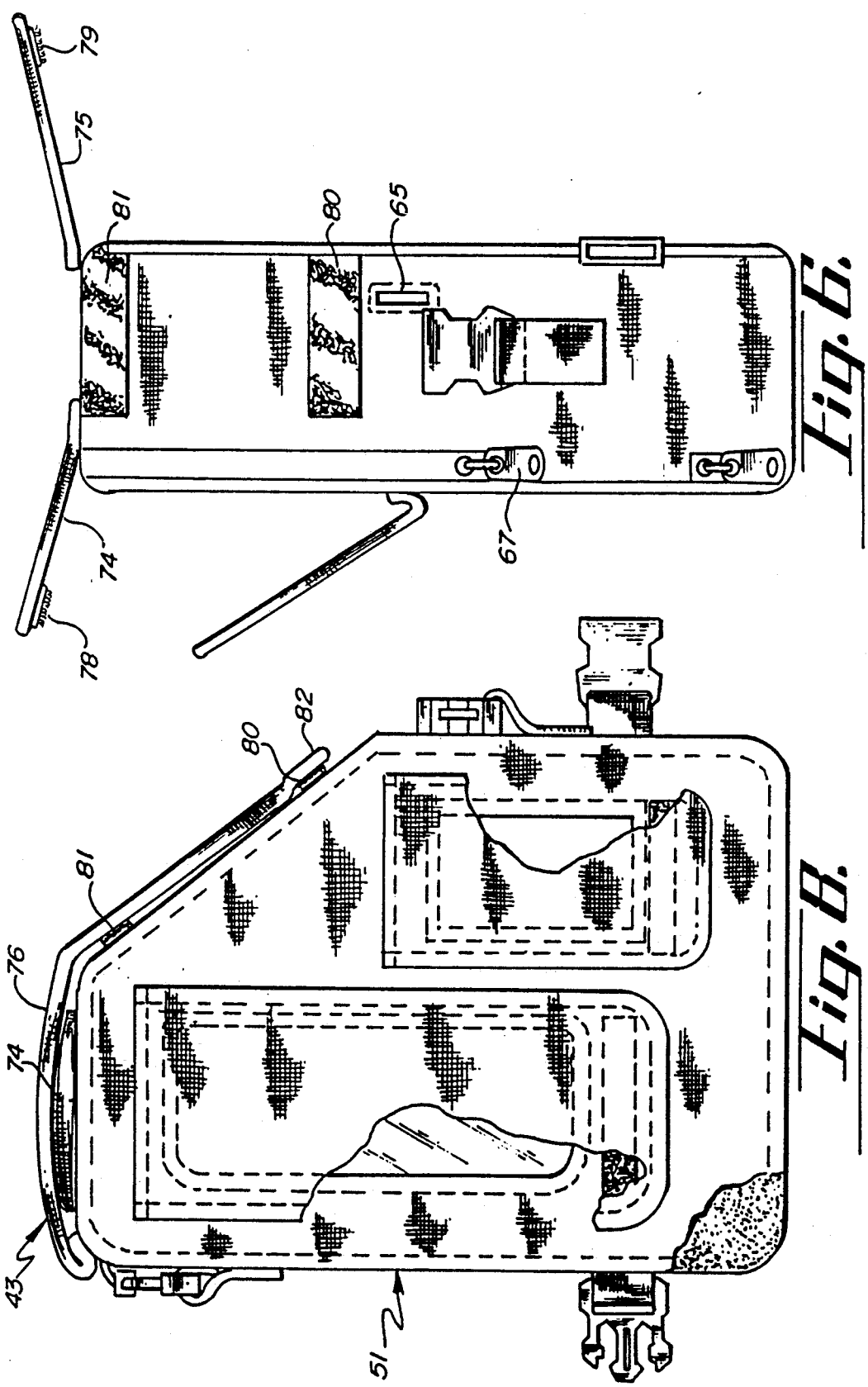

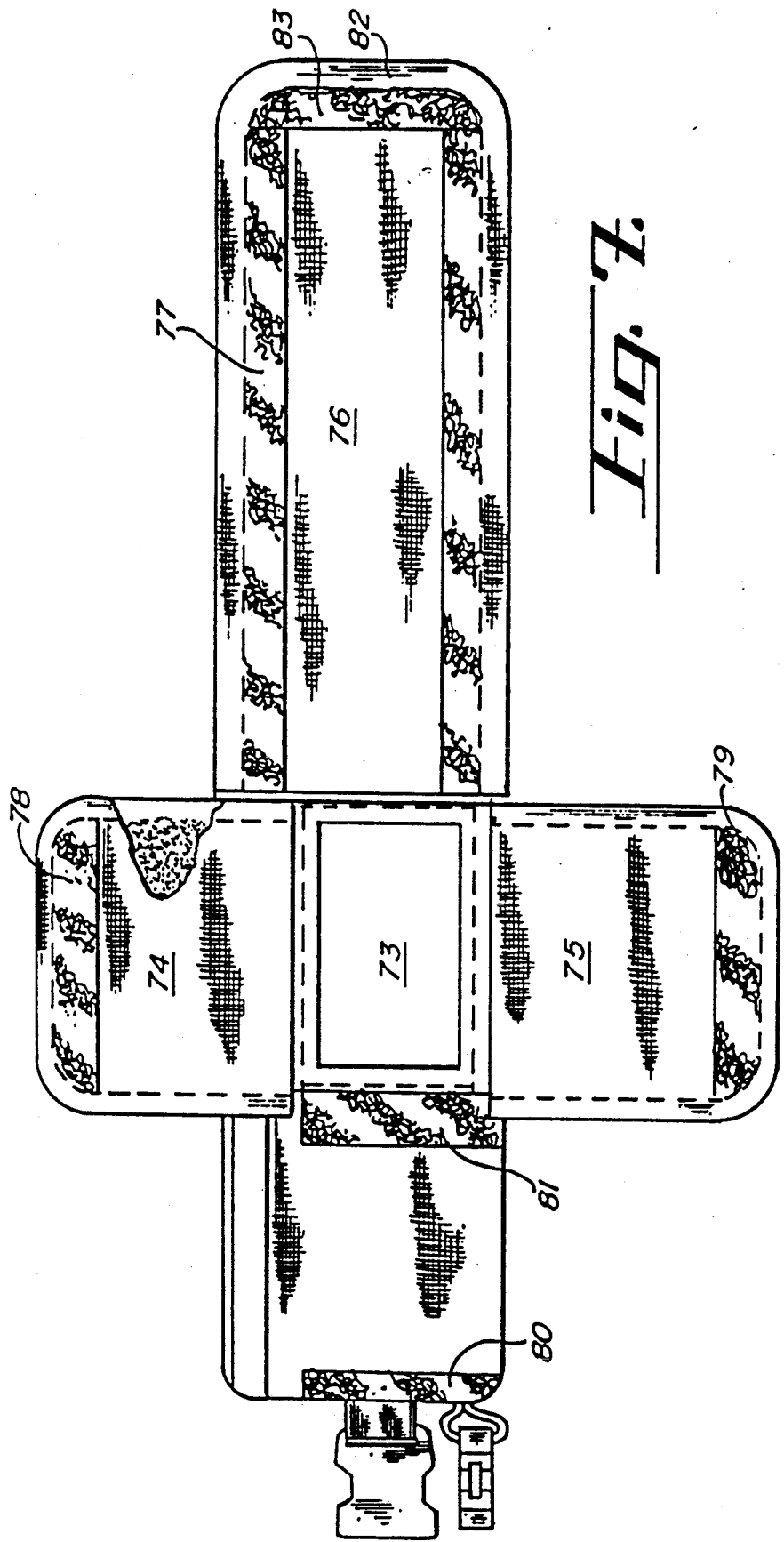

ADJUSTABLE CARRYING CASE FOR A FLUID DELIVERY SYSTEM

This application is a continuation-in-part of co-pending U.S. patent application Ser. No. 679,886 filed Apr. 3, 1991 titled "Support Device for a Fluid Delivery System and Case Therefore".

BACKGROUND OF THE INVENTION

1. Field of the Invention

This invention relates generally to ambulatory fluid delivery systems. More specifically, the present invention relates to a carrying case for a fluid delivery system mounted in a support device for supporting and protecting elements thereof, e.g. pump, fluid container, tubing, drip chamber, etc.

2. Description of the Prior Art

It is common for patient's having certain medical problems to require periodic premeasured infusions of fluid, such as medicaments or nutrients, into their bodies. Examples of such patients are those who may require nutrients to be delivered directly into their digestive tract periodically over long periods of time, or cancer patients who require exacting amounts of medication to be delivered intravenously at precise periods of time.

In the past, such patients required hospitalization in order to allow medical personnel to perform the infusions at the proper time and in the proper amounts. Such procedures were extremely time consuming to the patient and also the hospital personnel, and had the potential of human error in calculation of infusion dosages and injection time intervals.

An improvement on the above procedure has been to employ a programmable pump to insure that the patient automatically receives the proper infusion dosage at the proper time period, thus relieving medical personnel from constant monitoring of the patient and from worrying about infusion amounts and time tables. Although the programmable pump greatly relieves medical personnel of time consuming care to the patient, the patient nevertheless remains bound to the hospital bed during prolonged infusion periods.

A further improvement has been to develop an infusion system which can not only automatically infuse preset volumes of fluid into the patient on a predetermined time table, but also allow the patient to be ambulatory. U.S. Pat. No. 4,657,486 to Stempfle et al. U.S. Pat. No. 4,416,595 to Cromie, and U.S. Pat. No. 4,397,639 to Eschweiler et al. are exemplary of portable infusion systems of this type. Each discloses a portable infusion device which is automatically operable at selected time intervals to inject accurate amounts of fluid medication into a patient's body, and is also sufficiently compact and portable to allow the patient to be ambulatory while being attached to the infusion system.

U.S. Pat. No. 4,688,595 to Srebnik et al. is also exemplary of fluid delivery systems of this type. Srebnik discloses a delivery system which includes an integrally molded base to which elements of the delivery system, i.e., the pump, the fluid container, etc. can be attached. The base allows the entire fluid delivery system to be transportable as a unit and makes it possible for the patient to move about without the inconvenience of transporting a more cumbersome apparatus, such as a prior art type infusion system affixed to a pole mounted on wheels.

Although there has been improvement in portable fluid delivery systems in the past, there nevertheless remain several inadequacies. First, fluid infusion systems generally include a programmable pump and a fluid delivery set comprising a fluid container, tubing, pinch clamp, drip chamber, etc., all connected as an integral unit. The container of the fluid delivery set may be a flexible bag, a rigid glass or plastic bottle or a burette.

Standard fluid delivery sets (i.e. sets intended for non-ambulatory use) include rather long tubular extensions to allow the fluid container to be placed on an infusion pole while the distal end of the tube is attached to a pump located remotely from the container adjacent a bed ridden or non-ambulatory patient. These sets are generally ill suited for placement in a portable device such as that described by the above-mentioned prior art devices. This is because these prior art portable systems enclosed in carrying cases generally require significantly shorter tubing extension to operate properly. The excess tubing of a standard infusion set is cumbersome and inhibitive of proper operation of the prior art systems, and often cannot be used without the risk of becoming occluded or pinched off during ambulatory use. In fact, systems such as that shown by Stempfle et al., require a unique "non-standard" tubing design in order to allow the fluid delivery set to be properly attached to the pump. Modifications to the standard fluid delivery set have been found to be unsatisfactory in that they require the hospital or other facility to stock the "non-standard" fluid delivery sets for use in the ambulatory type systems, along with standard sets for all other uses. This becomes necessary since the "non-standard" ambulatory sets are generally unsuitable for use on "standard" non-ambulatory systems.

OBJECTS AND SUMMARY OF THE INVENTION

Briefly, and in general terms, the present invention provides for ambulatory use of a "standard" pump and fluid delivery set of a fluid delivery system while at the same time reliably preventing kinking or occlusion of excess tubing thereof along with other inadvertent damage to the system.

It is an object of the present invention to provide a portable fluid delivery system which is designed to accommodate standard fluid delivery sets therewith.

It is another object of the present invention to provide an ambulatory fluid delivery system which is designed to avoid occlusions or damage to the tubing of standard fluid delivery sets.

It is another object of the present invention to provide a support device and carrying case for a fluid delivery system which will allow use of standard fluid delivery sets (designed for non-ambulatory use) therein and which will protect and avoid occlusion of any excess tubing.

It is another object of the present invention to provide a support device and carrying case which is readily adjustable for use with soft bag, blow molded bottle, glass bottle, or burette-type fluid containers of fluid delivery sets.

It is a further object of the present invention to provide a support device and carrying case which allow for the pump of a fluid delivery system to be readily inserted or removed therefrom.

These and other objects of the present invention are realized in the following specific preferred embodiments thereof, disclosed for purposes of example and not by way of limitation, which comprise an adjustable carrying case and a rigid support device for holding the fluid delivery system. The support device includes a receptacle for receiving and locking a standard infusion pump in place therein, and an adjustable, generically-shaped area for receiving and retaining a container of a fluid delivery set in a fixed position relative to the pump. The support device also includes an elongated channel extending around a substantial portion of the perimeter of its rigid body into which the tubing of the fluid delivery set can be inserted. The elongate channel is designed to match the length of the tubing included on a "standard" fluid delivery set so that tubing between the container and the pump is protected against kinking or occlusion along its entire length. The rigid body also includes straps, brackets, and clamps which are strategically positioned to provide maximum support for anyone of several types of fluid containers, such as soft bags, glass bottles, blow molded plastic bottles, burettes, etc. The carrying case is preferably designed to enclose the support device alloy with the fluid delivery system, and to allow ready access to operation of the pump or visualization of fluid levels in the container of the delivery system. The case may include a strap or other type of handle to allow the patient to transport the entire fluid delivery system without concern for kinking or occlusion of the fluid set tubing, or for other damage to the system.

The carrying case is further designed to include an extendible "chimney" which allows the carrying case to be adapted for use with fluid sets having large fluid containers which require the clamp of the support device to be moved to its extended position. The extensible chamber is formed of a plurality of flaps which can be folded into a closed, non-extended, position when not in use, and can be unfolded into an extended position when needed to wrap around and encase an extended clamp of the support device when holding a large fluid container.

These and other objects and advantages of the present invention will become apparent from the following more detailed description, when taken in conjunction with the accompanying drawings in which like elements are identified with like numerals throughout.

BRIEF DESCRIPTION OF THE DRAWINGS

FIG. 1(b) is a side view of the support device of FIG. 1(a);

FIG. 1(c) is a side view of the support device of FIG. 1(a) opposite the side view of FIG. 1(b);

FIG. 6 is a right side view of the case of FIG. 5;

FIG. 7 is a top view of the case of FIG. 11(a);

FIG. 8 is a front view of the carrying case of FIG. 5, with the extension member closed in the non-use position.

DETAILED DESCRIPTION OF THE PREFERRED EMBODIMENTS

Figure 1A:
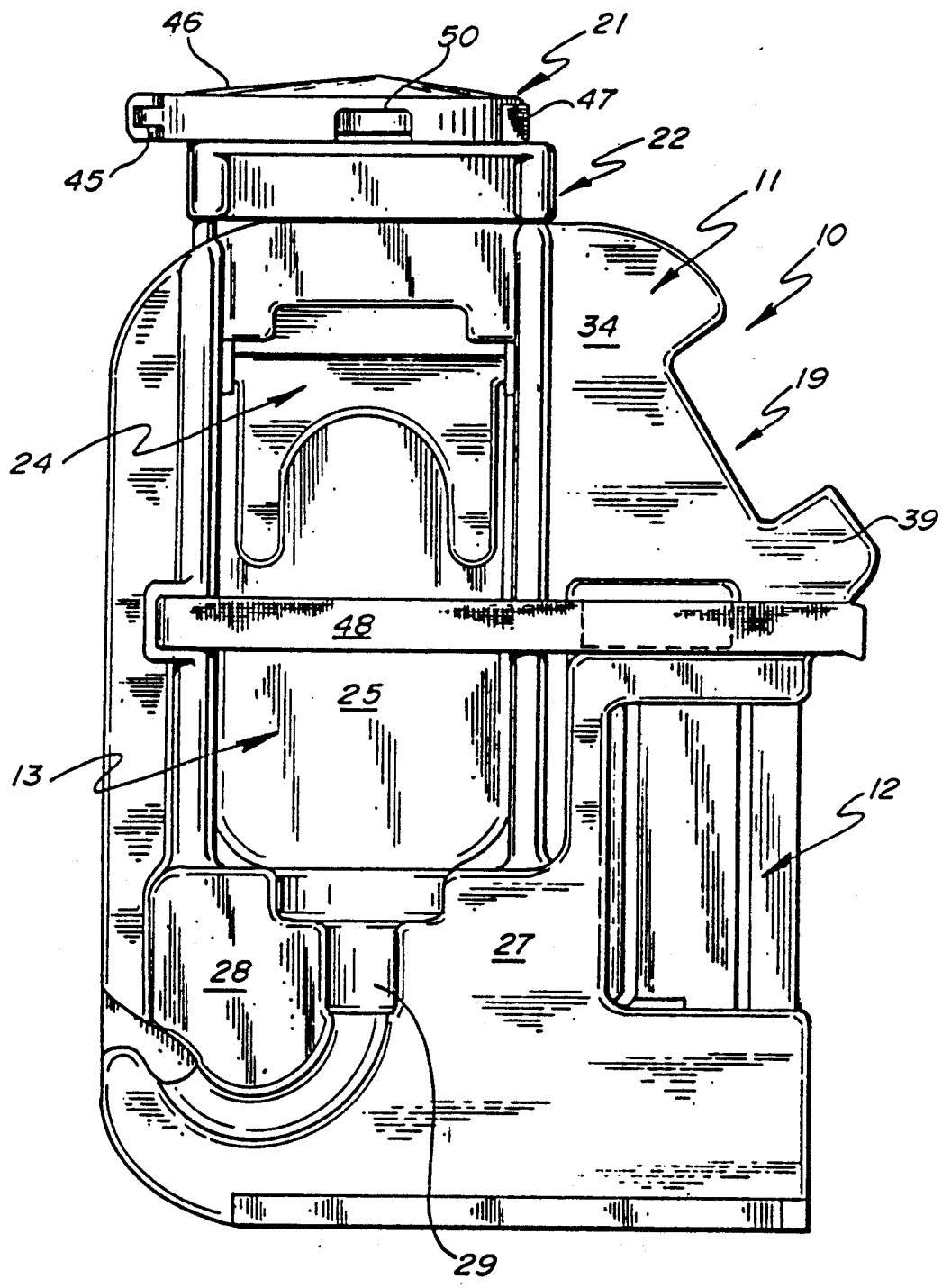
FIG. 1(a) is a front view of a support device made in accordance with the principles of the present invention.

As shown in the exemplary drawings for the purposes of illustration, an embodiment of a support device made in accordance with the principles of the present invention, referred to generally by the reference numeral 10, is provided for support of a standard (non-ambulatory type) fluid set and an infusion pump of a fluid delivery system.

More specifically, as shown in FIGS. 1(a)-(d) and FIG. 2, the support device 10 includes a generally rectangular rigid body 11 which is preferably formed of rigid polymeric material or other lightweight material such as wood, metal alloy, etc. The body 11 is adapted to receive and retain an infusion pump 15 and a fluid delivery set 16 of a fluid delivery system.

The body 11 forms a pump compartment 12 adapted to receive the standard infusion pump 15, a container compartment 13 adapted to partially receive a soft bag 17 from the standard fluid set 16, a tube channel 14 adapted to receive the tube 18 of the standard fluid set 16, and a pinch clamp compartment 19 adapted to receive a pinch valve 20 located on the tube 18 of the fluid set 16.

The support device 10 also includes a plurality of fastening elements which are adapted for use in securing the fluid delivery system to the rigid support body 11 during use. These elements include a lid clamp 21 which is permanently affixed to a lid clamp extension 22, a securing strap 23, a saddle bracket 24 which is secured in a flush mount position in the bottom 25 of container compartment 13, and a pump locking mechanism (not shown) formed as a part of the base 26 of the body 11. The body 11 is also integrally formed with an elevated section 27 which cooperates with a similarly elevated section 28 to form the tube path 29. Elevated section 27 also forms part of the pump compartment 12.

Finally, if desired, an extendable leg 30 may be located in elevated section 27 so as to be flush therewith when the leg 30 is in its retracted position, and to be perpendicular therewith and parallel to base 26 when in its extended position.

As best shown in FIGS. 1(a)-(c), the tube channel 14 of the support device 10 extends around approximately two thirds of the circumference of the body 11. The tube channel 14 is generally U-shaped in cross-section and includes a base 31, a front wall 32, and a back wall 33.

The tube channel 14 is essentially a channel between the front and back portions 34 and 35, respectively, of the body 11, and extends from entrance opening 36 across the top and partially down the opposite side of body 11 to exit opening 37. Slightly above exit opening 37, the channel 14 is interrupted by the pinch clamp compartment 19 which is sized to receive the standard type pinch valve 20 commonly attached to the tubing 18 of the fluid delivery set 16. The pinch clamp compartment 19 is formed by a cut out section of body 11, and is sufficiently large to allow the pinch clamp 20 (see FIG. 2) to rest therein when the tubing 18 is located in the tube channel 14.

The channel 14 is designed to allow accommodation of the tubing 18 of the fluid set 16 even though slight variation in tubing length may occur between sets 16. This is possible due to the channel 14 being formed to a sufficient depth to allow some "snaking" of the tube 18 when necessary for the channel 14 to be able to accommodate its entire length. Further, the channel 14 is also designed with a lip 38 which retains the tubing 18 therein once place, even though some "snaking" may occur.

As best illustrated in FIG. 1(c), the forward sloping section 39 of the body 11 causes the exit opening 37 of the tube channel 14 to be positioned somewhat centrally over the pump compartment 12. This is advantageous in that it allows the tubing 18 of the fluid delivery set 16 to exit channel 14 at exit opening 37 in the proper position for reception into the hinged pump arm 40 of the pump 30.

Figure 3:
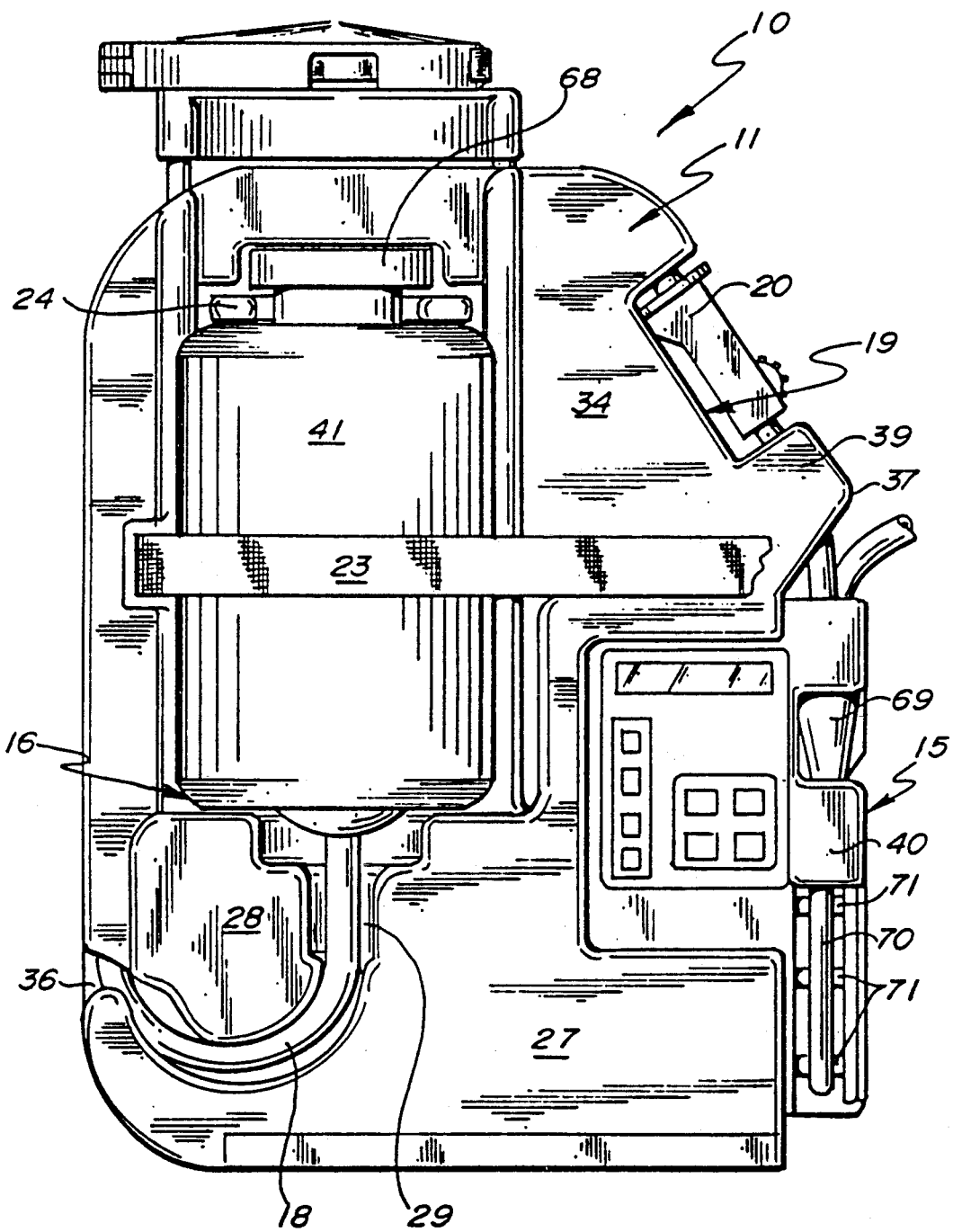
FIG. 3 is a front view of the support device of FIG. 1(a) including a pump and rigid bottle-type container of a fluid delivery set.

The support device 10 of the present invention is adapted to be able to receive and secure several different types of containers commonly used with standard fluid delivery sets 16. For example, as best shown in FIG. 1(c) and FIG. 3, container compartment 13 is recessed below front portion 34 of body 11, and shaped to receive a portion of a rigid blow molded type plastic bottle 41, with the assistance of the saddle bracket 21.

Alternatively, as best shown in FIGS. 1(a)–(c), the body 11 includes a lid clamp extension 22 on its front portion 34 which extends above the container compartment 13 and includes a lid clamp 21 oriented to receive the lid 42 of a soft flexible bag 17. The lid clamp 21 operates to secure the lid 42 of bag 17 in its proper position to allow the bag 17 to be properly located within container compartment 13. Also, and more importantly, the lid clamp 21 operates to prevent the sudden application of an external pressure from inadvertently bursting the lid 42 open during use, such as may occur if the support device 10 is inadvertently dropped.

As best shown in FIGS. 1(a) and 1(c), the lid clamp 21 includes a inner clamp jaw 44 which is permanently attached to the lid clamp extension 22, and permanently attached through hinge 45 to an outer clamp jaw 46. A strap 47 including a hook and pile type fastener 48, is attached to jaws 44 and 46. The strap 47 allows the clamp 21 to be securely fixed in a closed position.

When in the closed position, the jaws 44 and 46 of the clamp 21 form a circular opening for receiving the mouth and lid 42 of the bag 17. The circular opening of the inner clamp jaw 44 forms an inner lip channel (not shown), and similarly, the outer clamp jaw 46 forms an outer lip channel (not shown), which will receive the circumferential edges of mouth and lid 42 of the bag 17. Also, since the lid 42 generally includes an opening tab 49 thereon, the outer clamp jaw 46 is formed with an opening 50 through which the tab 49 can extend when the clamp 21 is closed about the lid 42.

Figure 2:
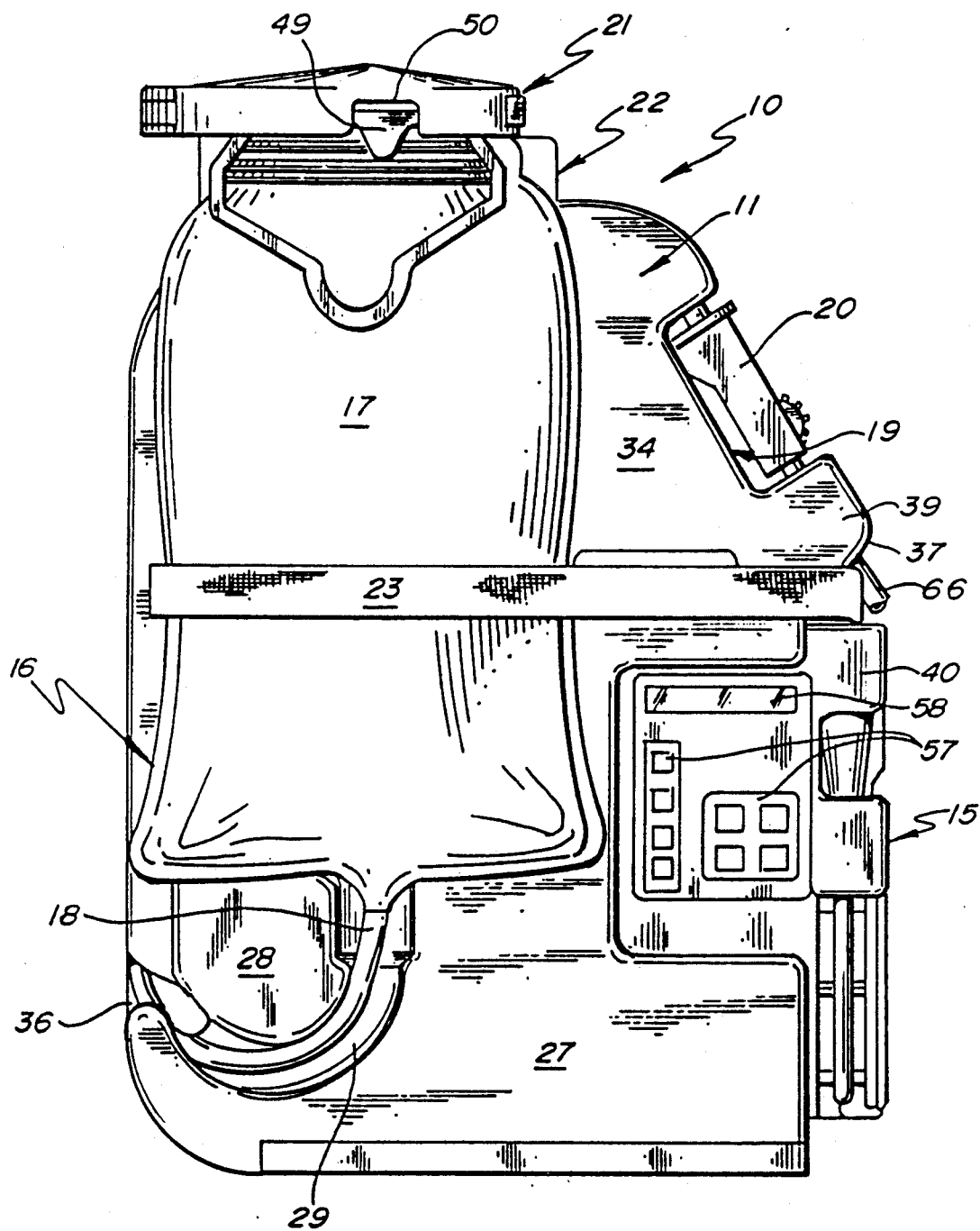
FIG. 2 is a front view of the support device of FIG. 1(a) including a pump and a soft bag-type container of a fluid delivery set.
Figure 4:
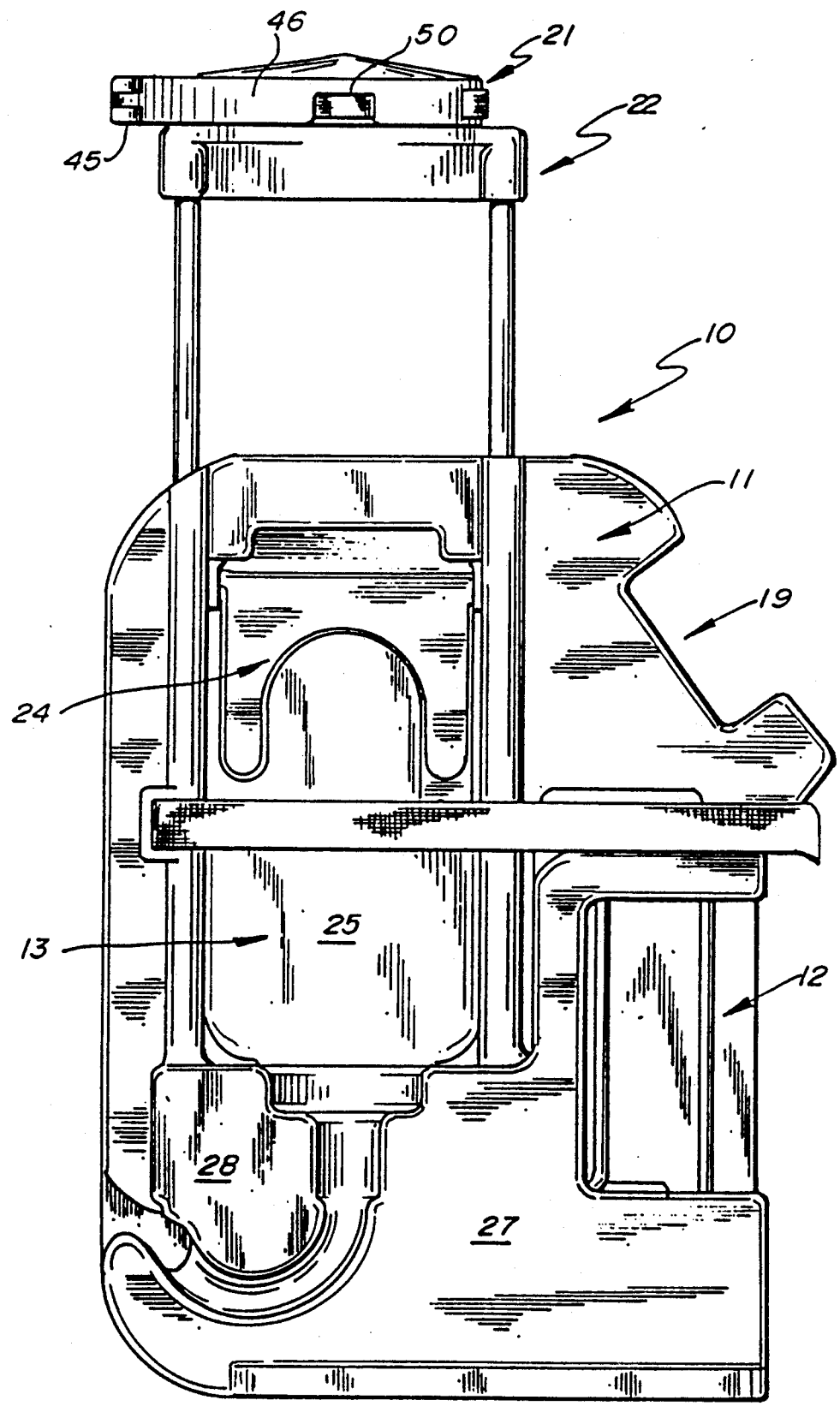
FIG. 4 is a front view of the support device of FIG. 1(a) with the lid clamp moved to its extended position.

The lid clamp 21 can be positioned above container compartment 13 a sufficient distance to allow the accommodation of the desired size of bag 17. For example, as shown in FIG. 2, the lid clamp extension 22 may be located adjacent the body 11 to allow the container compartment 13 to accept and properly position a bag 17 of standard 600 ml. volume. Alternatively, as shown in FIG. 4, the lid clamp extension 18 can be located a sufficient distance from body 11 to allow room in container compartment 13 to accept a bag 17 of the standard 1000 ml. volume.

A detailed description of the support device 10 of the present invention is given in co-pending application Ser. No. 679,886, filed Apr. 3, 1991, and is incorporated herein by reference.

Figure 5:
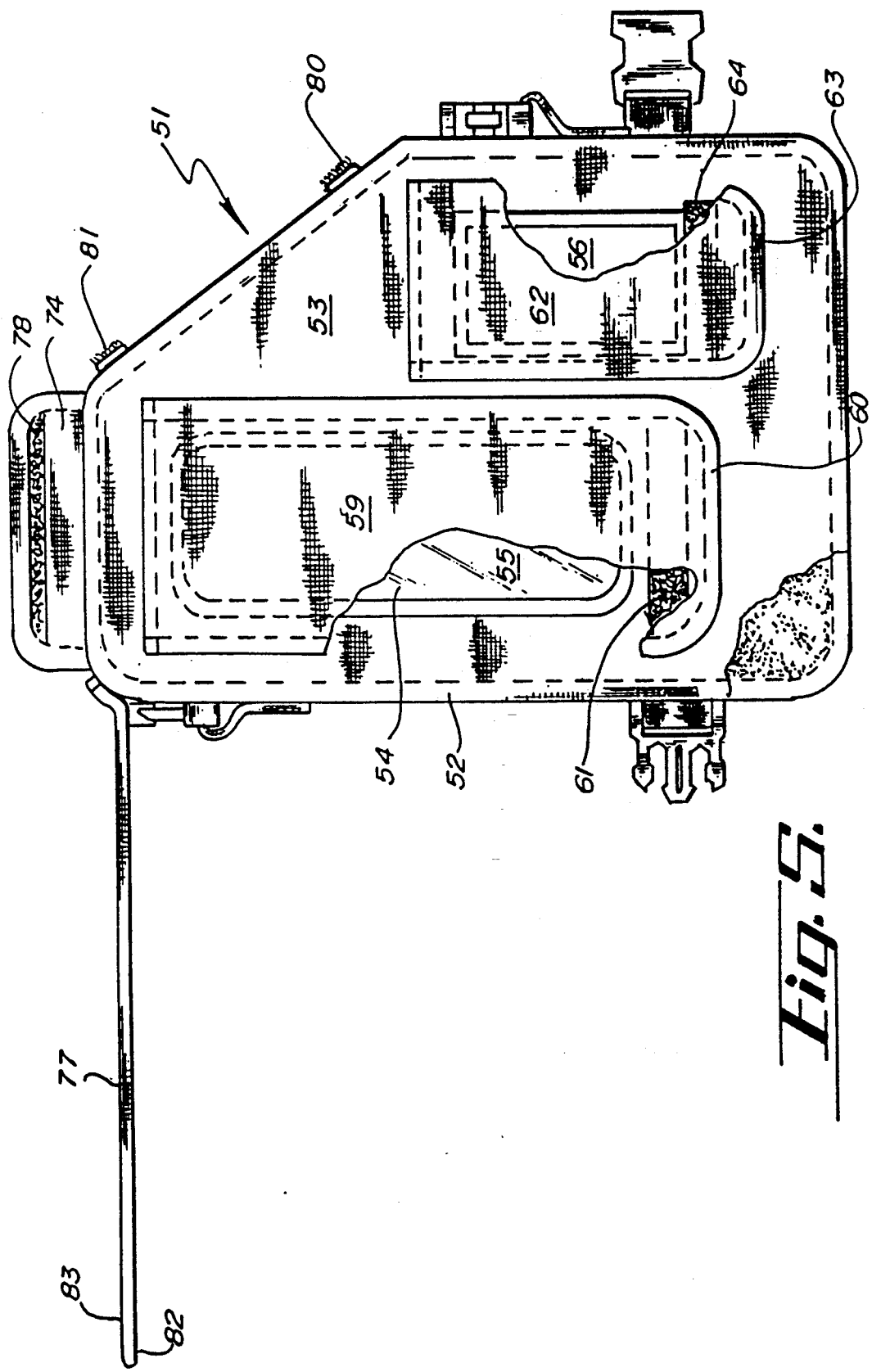
FIG. 5 is a front view of a preferred embodiment of a carrying case for protecting the fluid delivery system of the present invention.

As best shown in FIG. 5, the carrying case 51 is formed generally to conform to the exterior shape of the support device 10 and includes semi-rigid foam lined walls 52 and cover 53. The cover 53 of the case 51 includes a visual access opening 54, covered with a clear plastic panel 55, which allows visual access to the bag 17 when mounted to the support device 10 for use.

Front 53 of the case 51 also includes a control panel opening 56 which allows visual and physical access to the control panel 57 and display 58 of the pump 30.

The opening 54 is covered by a flap 59 which is sized so as to cover the entire opening 54 in a protective manner. The flap 59 can include an opening tab 60 and a fastening means such as hook and pile fasteners 61.

Control panel opening 56 also includes a flap 62 sized to completely cover the opening 56 to protect the pump 15. Flap 62 may also include an opening tab 63 and hook and pile type fastener 64. Further, flap 62 may also include a semi-rigid protection panel (not shown) which will supply added protection against accidental control panel activation, or damage to the pump 15, due to an inadvertent blow to the case 51.

The case 51 can include a carrying strap for allowing the case to be carried on the shoulder, back or around the waist of the patient while ambulatory.

As shown in FIG. 6, the case 51 further includes a tube outlet 65 to allow tubing 66 (see FIG. 3) exiting the pump 15 to pass outside of the case 51 and be attached to the patient.

The case 51 opens and closes in a "clam-shell" fashion, and may be secured in its closed position in any well known manner, such as by zipper 67 extending around the majority of the case's perimeter.

The case 51 as described above is described in more detail in co-pending U.S. application Ser. No. 679,886 filed Apr. 3, 1991 which is incorporated herein by reference. The case 51 of the present invention further includes an extension 43 which allows the case 51 to be adapted to the particular size necessary to accommodate the support device 10 in instances where the lid clamp extension 22 has been extended away from the rigid body 11 to accommodate a large bag 17 of a fluid delivery set 16.

As shown in FIGS. 5 through 7, the top of case 51 is formed with an opening 73 therethrough which is adapted to allow the lid clamp extension 22 to extend therethrough when in its extended position holding an enlarged bag 17 of a standard fluid set 16. Adjacent the opening 73 in diametrically opposed positions, are front side flap 74 and back side flap 75. Also adjacent opening 73, in a position aligned with the side surfaces of the bag 51 is a central flap 76. Flaps 74 and 75 are of a length which is substantially equal to the extension length of the lid clamp extension 22 of the support device 10. The central flap 76 is of a length which approximates the distance around the perimeter of the front and back side flaps 74 and 75 respectively.

When there is no need for extending the pack 51, e.g. when the lid clamp extension 22 is in the non-extended position relative to rigid body 11, and a small bag 17 is located in the support device 10, the front and back side flaps 74 and 75 are folded over the openings 73 and the central flap is then extended over the folded front and back side flaps 74 and 75 until the end 82 of the central flap 76 extends a sufficient distance around the side of the case 51 to allow end fastener 83 to attach with the closed position fastener 80 on the case 51.

Figure 9:
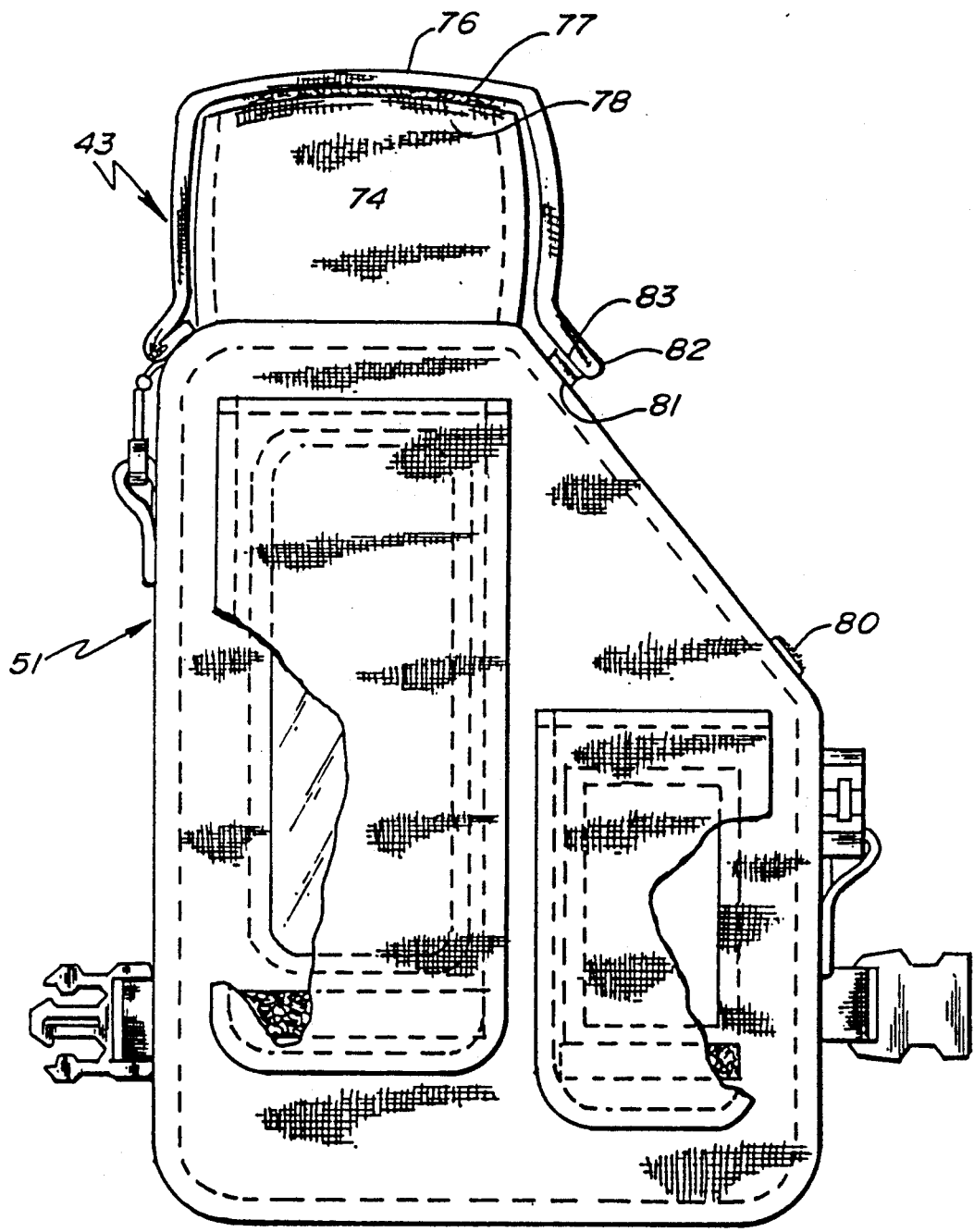
FIG. 9 is a front view of the carrying case of FIG. 5, with the extension member closed in its extended position.

When it is necessary to extend the case 51 to accommodate an extended lid clamp extension 22 and large bag 17, e.g. when lid clamp extension 22 is in its extended position relative to rigid body 11 for purposes of receiving a large bag 17, the front and back side flaps 74 and 75 respectively are extended vertically in the manner shown in FIG. 9, and the front and back side flap fasteners 78 and 79 respectively are folded inwardly so as to rest on top of the lid clamp extension 22. The central flap 76 is then extended over the lid clamp extension 22 and the central flap fastener 77 engages with the front and back flap fasteners 78 and 79 respectively. Extension of central flap 76 is continued until the end fastener 83 thereof engages with the open position fastener 81 located on the side of the case 51. In this position, the support device and the bag 17 are completely enclosed within the extension 43 of the case 51.

Referring now to FIG. 3, the method of attachment of a fluid delivery set 16 including the rigid bottle 41, and a pump 15 to the support device 10 of the present invention is described as follows. The pump 15 is inserted into pump compartment 12 until it is locked in position by the pump locking mechanism (not shown). The saddle bracket 24 is lifted to its "pop-up" position and the bottle 41 is inserted into the container compartment 13 until tubing 18 thereof can extend into the tube path 29. In this position, the bracket 24 secures the mouth and lid 68 of the bottle 41 against lateral movement. The strap 23 is then secured over bottle 41 to prevent its escape from the compartment 13. The tube 18 is then grasped and forced into entrance opening 36 of tube channel 14 and drawn the entire length of channel 14 until the pinch valve 20 is reached. The pinch valve 20 is then adjusted along tubing 18 until it is oriented properly to be received in pinch valve compartment 15. Tubing 18 is then extended through the remainder of tubing channel 14 and allowed to extend beyond exit 37.

Next, the drip chamber 69 is inserted into the open pump arm 40 of the pump 15 and pump tubing 70 is passed around the pump roller 71 until the retention ring 72 is properly positioned in a slot (not shown) within the arm 40 in such a manner as will cause the tube 70 to be stretched over the roller 71 of the pump 15 when the arm 40 is moved to its closed position.

The hinged pump arm 40 is then rotated into its closed and operating position and the outlet infusion tube 66 is extended away from the pump arm 40 toward the patient. The support device 10 may then be inserted into the carrying case 51 with the infusion tube 66 extending through the tubing outlet opening 65.

Alternatively, a fluid delivery set 16 including a soft bag 17 may be attached to the support device 10 in an manner similar to that described above with respect to the rigid bottle-type of fluid infusion set 16, except that the saddle bracket 24 is not used, and instead, the lid 42 of the bag 17 is inserted into the lid clamp 21 to be securely clamped in place on the body 11.

Similarly, a fluid infusion set 16 including a burette type container can be positioned in the support device 10 in a manner similar to that described above with the saddle bracket 24 being first rotated to its "snap up" position and the burette being placed in the bracket 24.

With each type of fluid infusion set 16, if desired or necessary, the strap 23 may be used to secure the container and the container compartment 13. Although not shown, other standard fluid sets 16, such as spike sets, etc. can be similarly used with the support device 10 of the present invention.

When the fluid infusion set 16 and pump 30 are properly attached to the support device 10, the entire device can then be inserted into a case 51 to simplify carrying the system during ambulatory use by the patient. As described above, the extension 43 of case 51 can be moved to its open position should a large bag 17 which requires the extension of the lid extension clamp 22 be presently attached to the support device 10.

It will be apparent from the foregoing, while particular embodiments of the invention have been illustrated and described, various modifications can be made thereto without departing from the spirit and scope of the present invention. Accordingly, it is not intended that the invention be limited, except as by the appended claims.

I claim:

1. A support device for a fluid delivery system including a fluid delivery set and a pump, the fluid delivery set including a fluid container and a tube for connection to the pump, said device comprising
    a body means having:
        a first compartment means for holding the pump,
        a second compartment means for holding the container,
    means for preventing kinking or occlusion of the tube between the container and the pump, and
    case means for enclosing said body means with said fluid delivery system attached thereto, said case means including an extension means and a holding means for holding said extension means adjacent said case means, said extension means being capable of being held closed in a non-extended position in which said extension means is held adjacent said case means by said folding means, and being capable of being opened to an extended position in which the interior volume of said means is modified.

2. A support device according to claim 1 wherein said means for preventing kinking or occlusion of the tube includes a third compartment means in said body for holding the tube, said third compartment means substantially enclosing the majority of the length of the tube between the container and the pump.

3. A support device according to claim 2 wherein said third compartment means is a channel extending around a substantial portion of a circumference of said body.

4. A support device according to claim 3 wherein said channel is generally U-shaped.

5. A support device according to claim 3 wherein said channel forms an elongated opening through which the tube can be inserted, and said opening includes means for resiliently deforming the tube as it passes into said channel.

6. A support device according to claim 4 wherein said means for resiliently deforming said tube is an elongated lip formed along at least a portion of said elongated opening of said channel.

7. A support device according to claim 1 wherein said second compartment means for holding the container is formed as a recess within a front surface of said body, said recess including a substantially flat bottom surface against which a portion of the container rests when properly placed in said second compartment means.

8. A support device according to claim 1 wherein said body means is formed of a rigid material.

9. A support device according to claim 1 wherein said body maintains said first compartment means, said second compartment means and said means for preventing kinking or occlusion of the tube, in fixed spaced relationship relative to each other.

10. A support device according to claim 1 include means attached to said body for securing the container in proper position within said second compartment means.

11. A support device according to claim 1 wherein said means for securing the container within said second compartment means includes strap means attached to said body and operable to partially surround a container located in said second compartment means to aid in securing said container in said compartment means.

12. A support device according to claim 1 wherein said means for securing the container in said second compartment means includes means for securing a substantial portion of a mouth and lid of the container in relatively fixed position relative to said body.

13. A support device according to claim 12 wherein said means for securing the mouth and lid of the container includes a clamp means attached to said body for substantially surrounding the mouth and lid of the container.

14. A support device according to claim 5 wherein said channel forms an inlet opening adjacent a first end of said elongated opening, and a exit opening adjacent a second end of said elongated opening, said inlet opening being located on said circumference of said body so as to conveniently receive the tube from the container when located in said second compartment means, and said exit opening being located on said circumference of said body adjacent said first compartment means so as to allow the tube to pass directly from said channel to the pump when located in said first compartment means.

15. A support device according to claim 2 wherein said body means includes a fourth compartment means, whereby, a pinch clamp included on a tube of a fluid delivery set may be located within said fourth compartment means when the tube is properly located within said third compartment means.

16. A support device according to claim 1 wherein said case means forms a first opening through which the container can be viewed when located within said case means, and a second opening through which said pump can be viewed when located within said case means.

17. A support device according to claim 16 wherein said case means further includes removable covering means for covering said first and second openings of said case means.

18. A support device according to claim 17 wherein said covering means for removably covering said second opening further includes a rigid stiffening member therein.

19. A support device according to claim 16 wherein said case means further includes a third opening through which said rigid body can be inserted and a cover means for securely closing said third opening.

20. A support device according to claim 1 wherein said case means is formed substantially of two similar halves reversibly separable by a fastening member whereby, said case means may be opened in clam-shell fashion to allow insertion of said rigid body means and subsequently reclosed by said fastening member.

21. A support device according to claim 1 wherein said extension means is located on said case means so as to accommodate at least a portion of said second compartment means of said body means.

22. A support device according to claim 1 wherein said extension means further includes a front side flap and a back side flap, and said extension means is capable of being formed into said non-extended position in which said front side flap and said back side flap are held adjacent said case means in said non-extended position by said central flap, and said extended position in which said front side flap and said back side flap are extended away from said case means in parallel relationship to each other and said central flap passes around the perimeter of each of said front side flap and back side flap to form an enclosed extension of said case means.

23. A support device according to claim 1 wherein said extension means includes an elongate central flap, and at least a portion of said holding means is formed on said elongate central flap.

24. A support device for a fluid delivery system including a fluid delivery set and a pump, the fluid delivery set including a fluid container and a tube for connection to the pump, said device comprising
a body means having:
a first compartment means for holding the pump,
a second compartment means for holding the container,
means for preventing kinking or occlusion of the tube between the container and the pump, and
case means for enclosing said body means with said fluid delivery system attached thereto, said case means including an extension means for modifying the interior volume of said case means, said extension means being located on said case means so as to accommodate at least a portion of said second compartment of said body means, said extension means being formed of a front side flap, a back side flap, and a central flap, and said extension means being capable of being formed into a non-extended position in which said front side flap and said back side flap are held adjacent said case means in said non-extended position by said central flap, and an extended position in which said front side flap and said back side flap are extended away from said case means in parallel relationship to each other and said central flap passes around the perimeter of each of said front side flap and back side flap to form an enclosed extension of said case means.

* * * * *